United States Patent [19]

Twist et al.

[11] Patent Number: 5,674,849
[45] Date of Patent: *Oct. 7, 1997

[54] ANTI-VIRAL COMPOSITIONS

[75] Inventors: Michael Twist, Toronto; Martin Sumner-Smith, Bolton, both of Canada

[73] Assignee: Allelix Biopharmaceuticals Inc., Mississauga, Canada

[*] Notice: The term of this patent shall not extend beyond the expiration date of Pat. No. 5,646,120.

[21] Appl. No.: 370,545

[22] Filed: Jan. 9, 1995

Related U.S. Application Data

[63] Continuation of Ser. No. 995,742, Dec. 22, 1992, abandoned, which is a continuation-in-part of Ser. No. 872,398, Apr. 23, 1992, abandoned, which is a continuation-in-part of Ser. No. 779,735, Oct. 23, 1991, abandoned, which is a continuation-in-part of Ser. No. 602,953, Oct. 24, 1990, abandoned.

[51] Int. Cl.$^6$ .................................................. A61K 38/08
[52] U.S. Cl. .......................... 514/15; 514/15; 514/16; 530/327; 530/328; 530/329
[58] Field of Search ................ 514/14–16; 530/327–329

[56] References Cited

U.S. PATENT DOCUMENTS

| | | | |
|---|---|---|---|
| 4,042,330 | 8/1977 | Deshmukh | 23/230 |
| 4,252,784 | 2/1981 | Levine | 424/9 |
| 4,447,356 | 5/1984 | Olivera | 260/112.5 |
| 4,713,366 | 12/1987 | Stevens | 514/13 |
| 4,837,304 | 6/1989 | Garsky et al. | 530/328 |
| 4,845,195 | 7/1989 | Colonno et al. | 530/330 |
| 5,021,437 | 6/1991 | Blumenkopf | 514/357 |
| 5,093,317 | 3/1992 | Lewis | 514/12 |
| 5,110,799 | 5/1992 | Tolman | 514/19 |
| 5,110,802 | 5/1992 | Cantin et al. | 514/44 |
| 5,114,711 | 5/1992 | Bell | 429/85.1 |
| 5,166,320 | 11/1992 | Wu et al. | 530/395 |
| 5,171,838 | 12/1992 | Chiba | 530/326 |
| 5,175,165 | 12/1992 | Blumenkopf | 514/262 |

FOREIGN PATENT DOCUMENTS

8912461  12/1989  WIPO .......................... A61K 39/12

OTHER PUBLICATIONS

Docherty *Antimicrob Agents Chemother.* 31, 1562, 1987.
Coy *Bioch Biophys Res Comm* 73 632, 1976.
Weeks, *Science* 249, 1281, 1990.
Elion, "Mechanism of Action and Selectivity of Acyclovir," *The American Journal of Medicine*, vol. 73, No. 1A, pp. 7–13 (1982).

Ratner et al., "Complete Nucleotide Sequence of the AIDS Virus, HTLV–III," *Nature*, vol. 313, pp. 277–284, (Jan. 1985).

Nahata, "Antiviral Drugs: Pharmacoknetics, Adverse Effects, and Therapeutic Use," *Journal of Pharmacy Technology*, vol. 3, pp. 100–108 (May/Jun. 1987).

Green et al., "Autonomous Functional Domains of Chemically Synthesized Human Immunodeficiency Virus Tat Trans–Activator," *Cell*, vol. 55, pp. 1179–1188 (Dec. 1988).

Ruben et al., "Structural and Functional Characterization of Human Immunodeficiency Virus tat Protein," vol. 63, No. 1, pp. 1–8 (Jan. 1989).

Hauber et al., "Mutational Analysis of the Conserved Basic Domain of Human Immunodeficiency Virus tat Protein," *Journal of Virology*, vol. 63, No. 3, pp. 1181–1187 (Mar. 1989).

Green et al., "Mutational Analysis of HIV–1 Tat Minimal Domain Peptides: Identification of Trans–Dominant Mutants That Suppress HIV–LTR–Driven Gene Expression," *Cell*, vol. 58, pp.215–223 (Jul. 1989).

M. Kuppuswamy et al., "Multiple Functional Domains of Tat, the trans–activator of HIV–1, Defined by Mutational Analysis," *Nucleic Acids Research*, vol. 17, No. 9, pp. 3551–3561 (1989).

Frankel et al., "Activity of Synthetic Peptides from the Tat Protein of Human Immunodeficiency Virus Type 1," *Proc. Nat'l. Acad. Sci. USA*, vol. 86, pp. 7397–7401 (Oct. 1989).

Arnold, Jr., "Polylysin–Drug Conjugates," *Methods in Enzymology*, vol. 112, pp. 270–285 (1985).

Weeks et al., "Fragments of the HIV–1 Tat Protein Specifically Bind TAR RNA," *Science*, vol. 249, pp. 1281–1285 (1990).

Roy et al., "A Bulge Structure in HIV–1 TAR RNA is Required for Tat Binding and Tat–Mediated trans–Activation," *Genes and Development*, vol. 4, pp. 1365–1373 (1990).

*Primary Examiner*—Cecilia J. Tsang
*Assistant Examiner*—David Lukton
*Attorney, Agent, or Firm*—Foley & Lardner

[57] ABSTRACT

An anti-viral composition includes a synergistic combination of an anti-viral nucleoside analogue, which may inhibit a virus-specific enzyme, such as viral thymidine kinase and reverse transcriptase, an anti-viral oligonucleotide compound having from 6 to 12 amino acid residues substantially all of which are D-arginine residues, and a pharmaceutically acceptable carrier. A method for treating a viral infection is also described.

14 Claims, 6 Drawing Sheets

ANTI-VIRAL COMPOSITIONS

This application is a continuation of application Ser. No. 07/995,742, filed Dec. 22, 1992, now abandoned, which is a CIP of application Ser. No. 07/872,398 filed Apr. 23, 1992, now abandoned, which is a CIP of application Ser. No. 07/779,735 filed Oct. 23, 1991, now abandoned, which is a CIP of application Ser. No. 07/602,953 filed Oct. 24, 1990 (abandoned).

FIELD OF THE INVENTION

The present invention relates to anti-viral compositions. In particular, the present invention relates to compositions containing a synergistic combination of an anti-viral nucleoside analogue and an anti-viral oligopeptide.

BACKGROUND OF THE INVENTION

Typically, anti-viral agents are modelled to inhibit viral replication within an infected cell. Viral replication may be prevented by down-regulation or inhibition of a protein required in the viral replication pathway, or by interference with the translocation of proteins and viral nucleic acid within the cell. Effective anti-viral agents specifically target steps within the viral replication pathway thereby inhibiting or hindering viral replication within infected host cells while having a minimal cytotoxic effect on the host. Thus, many anti-viral agents are specific inhibitors to virus-specified enzymes and proteins, such as viral DNA and RNA polymerases, virus-specific thymidine kinase and cleavage enzymes for viral capsid protein. Nucleoside analogues, for example, have been developed which target particular enzymes in the viral replication pathway by mimicking a natural substrate of the enzyme.

Adverse toxicity effects exist with the administration of most anti-viral agents, particularly at the dosage levels required to attain effective antiviral chemotherapy, due to a lack of viral specificity. The adverse effects associated with the administration of some anti-viral agents are not as severe as those associated with other agents; nonetheless, such adverse effects do exist. Presently, there are very few anti-viral agents which are considered to be efficacious i.e. agents having a high level of viral toxicity and a low level of cytotoxicity. Such agents include iododeoxyuridine, adenine arabinoside and trifluorothymidine, all used to treat herpetic keratitis, acyclovir which is used in the treatment of genital herpes and mucosal and cutaneous herpes infections in the immunocompromised patient, and amantadine which is used to treat influenza A. These anti-viral agents have a relatively low level of cytotoxicity in comparison to other anti-viral agents. The adverse toxicity effects associated with acyclovir, for example, include transient impairment of renal function, inflammation at the site of injection, nausea and vomiting, reversible neurological reactions, raised liver enzymes, rashes and increased hematological indexes.

It would be desirable to eliminate, or at least minimize, the cytotoxicity associated with the administration of anti-viral agents otherwise determined to be effective. It is generally recognized that the toxicity of an anti-viral agent may be avoided or at least minimized by administration of a reduced dose of the anti-viral agent; however, it is also recognized that the effectiveness of an anti-viral agent generally decreases as the dose is reduced.

SUMMARY OF THE INVENTION

It is an object of the present invention to provide a novel anti-viral composition, and a method of treating mammals having a viral infection.

Accordingly, in one of its aspects, the present invention provides a composition for treating a viral infection comprising a pharmaceutically acceptable carrier and a synergistic combination of 1) a nucleoside analogue that inhibits said viral infection; and
2) an anti-viral oligopeptide compound of the formula (I):

$$R1-[X]-R2 \qquad (I)$$

wherein X represents an oligopeptide consisting of from about 6 to 12 amino acid residues substantially all of which are D-arginine resides, R1 is H or an N-terminal protecting group and R2 is OH or a C-terminal protecting group.

In another aspect of the present invention, there is provided a composition for treating a herpesvirus infection comprising a pharmaceutically acceptable carrier and a synergistic combination of 1) a nucleoside analogue that inhibits said herpesvirus; and
2) an anti-viral oligopeptide compound of the formula (I):

$$R1-[X]-R2 \qquad (I)$$

wherein X represents an oligopeptide consisting of from about 6 to 12 amino acid residues substantially all of which are D-arginine resides, R1 is H or an N-terminal protecting group and R2 is OH or a C-terminal protecting group.

In a further aspect of the present invention, a composition for treating an HIV infection is provided comprising a pharmaceutically acceptable carrier and a synergistic combination of 1) a nucleoside analogue that inhibits HIV; and
2) an anti-viral oligopeptide compound of the formula (I):

$$R1-[X]-R2 \qquad (I)$$

wherein X represents an oligopeptide consisting of from about 6 to 12 amino acid residues substantially all of which are D-arginine resides, R1 is H or an N-terminal protecting group, and R2 is OH or a C-terminal protecting group.

In a further aspect of the present invention, a pharmaceutical combination in kit form is provided including:

a pharmaceutical nucleoside analogue composition comprising an anti-viral nucleoside analogue and a pharmaceutically acceptable carrier; and a pharmaceutical oligopeptide composition comprising an anti-viral oligopeptide compound of the formula (I):

$$R1-[X]-R2 \qquad (I)$$

wherein X represents an oligopeptide consisting of from about 6 to 12 amino acid residues substantially all of which are D-arginine resides, R1 is H or an N-terminal protecting group, and R2 is OH or a C-terminal protecting group, and a pharmaceutically acceptable carrier.

BRIEF REFERENCE TO THE DRAWINGS

Embodiments of the invention will be described by way of example only by reference to the following figures in which.

DETAILED DESCRIPTION OF THE INVENTION

It has been found that the combination of an anti-viral nucleoside analogue and an anti-viral oligopeptide compound comprising from about 6 to about 12 amino acid residues, substantially all of which are D-arginine residues, is a synergistic combination in which the cumulative anti-viral activity of the anti-viral nucleoside analogue and the anti-viral oligopeptide is surpassed. Synergistic compositions according to the present invention, thus, may advantageously comprise lower doses of the active anti-viral nucleoside analogue while maintaining a level of anti-viral activity that is characteristic of a higher dose thereof. As a result, the cytotoxicity typically associated with the administration of an anti-viral nucleoside analogue may be minimized by the administration of compositions according to the present invention. Alternatively, the present synergistic compositions may comprise a typically administered dosage of anti-viral nucleoside analogue in combination with an anti-viral oligopeptide as herein defined to achieve a level of anti-viral activity which is greater than that normally required while maintaining an acceptable level of cytotoxicity. Such an increased level of anti-viral activity is useful particularly in the treatment of a viral infection caused by a strain that has developed a resistance to the administered nucleoside analogue.

The relative amounts of nucleoside analogue and oligopeptide required to obtain a synergistic composition are determined using assays of conventional design, as described herein. The term "synergistic" as it is used herein with respect to combinations and compositions is meant to encompass compositions according to the present invention which display anti-viral activity in excess of the cumulative anti-viral activity expected by combining the anti-viral components of the present invention, i.e. the nucleoside analogue and oligopeptide.

The synergistic effect of the anti-viral oligopeptide compound has been identified to amplify the activity of anti-viral nucleosides targeted against a broad spectrum of viruses including both DNA viruses and RNA viruses. Examples of viruses encompassed within the "DNA virus" classification include but are not limited to viruses of the "herpesvirus" family, a family including viruses which are morphologically similar to herpes simplex viruses and specifically encompassing those viruses which are enveloped, double-stranded DNA viruses. Included within this family of viruses are herpes simplex virus 1 (HSV-1), herpes simplex virus 2 (HSV-2), varicella-zoster virus, Epstein-Barr virus (EBV) and cytomegalovirus (CMV). Examples of viruses encompassed within the "RNA virus" classification include retroviruses, i.e. viruses having a single-stranded RNA genome, such as HIV-1, HIV-2, SIV-1 and HTLV-1, the various strains thereof and other viruses related thereto.

A suitable anti-viral nucleoside analogue is combined with an anti-viral oligopeptide as described herein to form a synergistic anti-viral composition. The term "nucleoside analogue" as used herein is meant to encompass analogues of both purine (i.e., adenine and guanine) and pyrimidine (i.e. thymine, uracil and cytosine) nucleosides which do not naturally exist within a cell. Such analogues may be in the oxy- or deoxy- forms similar to the nucleosides that naturally exist in both RNA and DNA. The terms "anti-viral nucleoside analogue" and "nucleoside analogue" are used interchangeably herein.

Appropriate nucleoside analogues are not restricted to analogues having a particular mode of anti-viral action; however, it is essential that such analogues do exhibit anti-viral activity. Preferably, the nucleoside analogue is virus-specific and, as such, specifically inhibits a viral protein or enzyme unique thereto which catalyzes a step in the viral replication pathway. In this way, cytotoxicity of the present composition is minimized. Enzymes such as virus-specific thymidine kinase and reverse transcriptase are examples of viral enzymes that may be targeted by the nucleoside analogue. Accordingly, a nucleoside analogue which inhibits one of these enzymes is an example of an analogue suitable for incorporation into the present composition.

Purine nucleoside analogues suitable for combination with an anti-viral oligopeptide to yield a synergistic composition include, but are not limited to, analogues of the purine nucleoside inosine such as dideoxyinosine (ddI) and analogues of guanosine such as those commonly known as acyclovir, ganciclovir, penciclovir and famciclovir. Of these guanosine analogues, acyclovir is the most widely used and has the following chemical structure:

Ganciclovir, also relatively common in the art, differs from acyclovir in that the {2-hydroxyethoxy}methyl group at the 9-position of the acyclovir is replaced by a {1,3-dihydroxy-2-propoxy}methyl as follows:

In a specific embodiment of the present invention, the present composition comprises acyclovir in combination with an anti-viral oligopeptide to form a synergistic composition. When administered independently, acyclovir is believed to react specifically with virus-induced thymidine kinase as described by Elion, AM. J. Med., 1982, 73(1A):7.

Generally, thymidine kinase phosphorylates nucleosides to form monophosphate nucleotides which are phosphorylated further by other enzymes. Acyclovir is phosphorylated specifically by viral thymidine kinase to become monophosphorylated and is subsequently converted into its diphosphate form by cellular guanylate kinase. Phosphorylation of the diphosphate to form the triphosphate is catalyzed by additional cellular enzymes. Triphosphorylated acyclovir specifically inhibits viral DNA polymerase by competing with deoxyguanosine triphospate. Additionally, the acyclovir triphosphate is a DNA chain terminator and upon its incorporation into a DNA molecule, further DNA synthesis is prevented. When combined with the anti-viral oligopeptide, the inhibitory activity of acyclovir is amplified. As described herein in detail in the specific examples, the inhibitory effect of the acyclovir/oligopeptide combination is greater than the expected cumulative inhibitory effect of these components.

Pyrimidine nucleoside analogues are also suitable for combination with an anti-viral oligopeptide to form synergistic anti-viral compositions, and include, for example, thymidine analogues such as azidothymidine (AZT) and cytodine analogues such as dideoxycytidine (ddC) and 2'-deoxy-3'-thiacytidine (3TC). In particular, AZT is noted for its activity against HIV-1 and in its capacity as an anti-viral agent, AZT inhibits the HIV reverse transcriptase enzyme which catalyzes the synthesis of DNA from viral RNA. AZT has the following chemical formula:

Thus, in another specific embodiment of the present invention, the present composition comprises AZT in combination with an anti-viral oligopeptide to yield a synergistic anti-viral composition against HIV1. As with the acyclovir/anti-viral oligopeptide combination, the AZT/anti-viral oligopeptide combination exhibits an anti-viral effect which exceeds the expected cumulative anti-viral effect of AZT and the anti-viral oligopeptide as determined by combining the individual anti-viral effect of each.

A synergistic composition results when the selected anti-viral nucleoside analogue is combined with an anti-viral oligopeptide compound having the formula (I):

in which R1 is H or an N-terminal protecting group, R2 is OH or a C-terminal protecting group and X represents an oligopeptide consisting of from 6 to 12 amide-linked amino acid residues substantially all of which are D-arginine. As used throughout, the term "substantially all" is meant to encompass D-arginine homopolymers, as well as encompassing those oligopeptides which comprise D-arginine residues and a single residue other than D-arginine, such as, for example, a glutamine or a lysine residue. Such anti-viral oligopeptides, and methods for obtaining them, are described in detail in co-pending U.S. patent application Ser. No. 779,735 now abandoned (corresponding to published PCT application no. WO 92/07871) and U.S. patent application No. 872,398, now abandoned both of which are incorporated herein by reference.

As used herein, the term "anti-viral oligopeptide compound" refers to an oligopeptide compound as defined above which independently exhibits anti-viral activity. Accordingly, the anti-viral activity of such oligopeptides is not dependent on the presence of an anti-viral agent, for example, an anti-viral nucleoside analogue.

Preferred oligopeptides for incorporation into the composition of the present invention include homopolymers of D-arginine, comprising from 6 to 12 D-arginine residues, and preferably comprising 9 D-arginine residues. An especially preferred oligopeptide for incorporation into a composition according to the present invention is a homopolymer comprising 9 D-arginine residues including an N-terminal protecting group and a C-terminal protecting group, e.g. acetyl-[(D-Arg)$_9$]-NH$_2$.

The term "N-terminal protecting group" refers to a radical group attached to the nitrogen of the amino terminus of the oligopeptide and serves to prevent reaction or chemical attack from occurring at the amino terminus. The term "C-terminal protecting group" refers to a radical group attached either to the oxygen or the carbon of the terminal carboxyl group of the oligopeptide and serves to prevent reaction or chemical attack from occurring at the carboxyl terminus.

Any chemical group which serves to protect peptide N- and C-terminal ends from reacting can be used to make an oligopeptide of the present invention. The N- and C-terminal protecting groups suitable for use in the preparation of the oligopeptides of the present invention must be appropriate in the pharmaceutical sense as the N- and C-protected oligopeptides are to be administered to mammals in some form to treat infection. Appropriate N-terminal protecting groups include lower alkanoyl groups of the formula R—C(O)— wherein R is a linear or branched lower alkyl having from 1 to 5 carbon atoms. Amino acid analogues lacking the amino functionality are also useful N-terminal protecting groups. A preferred N-terminal protecting groups is acetyl, CH$_3$C(O)—. With respect to protection of the C-terminus, the carboxyl group of the terminal amino acid may be incorporated into the protecting functionality. This is the case when protecting groups such as esters, ketones or amides are used. Thus, examples of useful carboxyl protecting groups are ester-forming alkyl groups, particularly lower alkyl groups such as methyl, ethyl and propyl; amide-forming amino groups such as primary amines (—NH$_2$); and monoalkylamino and dialkylamino groups such as methylamino, ethylamino, dimethylamino, diethylamino, methylethylamino and the like. Amino acid analogues lacking the carboxyl functionality are also useful C-terminal protecting groups such as agmatine.

Oligopeptides of the present invention may be readily prepared by standard, well-established solid-phase peptide synthesis (SPPS) as described by Stewart et al. in *Solid Phase Peptide Synthesis*, 2nd Edition, 1984, Pierce Chemical Company, Rockfor, Ill.; and as described by Bodanszky and Bodanszky in *The Practice of Peptide Synthesis*, 1984, Springer-Verlag, New York. At the outset, a suitably protected amino acid residue is attached through its carboxyl group to a derivatized, insoluble polymeric support, such as cross-linked polystyrene or polyamide resin. "Suitably protected" refers to the presence of protecting groups on both the α-amino group of the amino acid, and on any side chain functional groups. Side chain protecting groups are generally stable to the solvents, reagents and reaction conditions used throughout the synthesis, and are removable under conditions which will not affect the final peptide product. Stepwise synthesis of the oligopeptide is carried out by the removal of the N-protecting group from the initial amino acid, and coupling thereto of the carboxyl end of the next amino acid in the sequence of the oligopeptide. This amino acid is also suitably protected. The carboxyl of the incoming amino acid can be activated to react with the N-terminus of the bound amino acid by formation into a reactive group such as formation into a carbodiimide, a symmetric acid anhydride or an "active ester" group such as hydroxygenzotriazole or pentafluorophenyl esters.

The preferred solid phase peptide synthesis methods include the OBC method which utilizes tert-butyloxycarbonyl as the α-amino protecting group, and the FMOC method which utilizes 9-fluorenylmethyloxycarbonyl to protect the α-amino of the amino acid residues, both methods of which are well-known by those of skill in the art.

N- and/or C-protecting groups can be incorporated into the oligopeptide using protocols conventional to SPPS methods. The C-terminal protecting group may be incorporated into the oligopeptide by using a solid phase which is adapted such that on cleavage of the oligopeptide from the supporting resin, the C-terminus retains thereon as a protecting group the resin ligand used to attach the initial amino acid of the peptide to the resin. To provide an oligopeptide having a primary amino C-terminal protecting group, for example, oligopeptide synthesis is carried out using a p-methylbenzhydrylamine (MBHA) resin. On cleavage of the synthesized oligopeptide, treatment with hydrofluoric acid releases a C-terminally amidated peptide. Likewise, an N-terminal protecting group can be incorporated on the oligopeptide while still attached to the resin. Treatment of the resin-attached oligopeptide with a suitable anhydride and nitrile will incorporate thereon an N-protecting group. To acetylate the N-terminus of the oligopeptide, the oligopeptide is treated with 20% acetic anhydride in acetonitrile. The N-protected oligopeptide is then cleaved from the resin, the side-chain protecting groups are removed and the oligopeptide is isolated.

The peptide must be purified once it has been synthesized, cleaved from the resin and suitably deprotected. For purification purposes, there are many standard methods that may be employed including reversed-phase high-pressure liquid chromatography (HPLC) using an alkylated silica column such as $C_4$-, $C_8$- or $C_{18}$-silica. A gradient mobile phase of increasing organic content is generally used to achieve purification, for example, acetonitrile in an aqueous buffer, usually containing a small amount of trifluoroacetic acid. Ion-exchange chromatography can also be used to separate peptides based on their charge.

In order to ensure that the peptide obtained is the desired oligopeptide for use in compositions of the present invention, analysis of the peptide composition may be carried out. Such composition analysis may be conducted using high resolution mass spectrometry to determine the molecular weight of the peptide. Alternatively, the amino acid content of the peptide can be confirmed by hydrolyzing the peptide in aqueous acid, and separating, identifying and quantifying the components of the mixture using HPLC, or an amino acid analyzer. Protein sequenators, which sequentially degrade the peptide and identify the amino acids in order, may also be used to determine definitely the sequence of the peptide.

To be suitable for use in the compositions of the present invention, the oligopeptide must be of "pharmaceutical grade" purity so as to be suitable for administration to a mammal in the treatment of viral infection. Accordingly, the oligopeptide must exhibit a uniform and authentic amino acid composition and sequence and must not include extraneous peptide material. Furthermore, the oligopeptide must meet the criteria as set out by national pharmaceutical regulatory bodies.

Compositions according to the present invention may be in any form suitable for administration. Such administrable forms include tablets, pills, capsules, powders, aerosols, suppositories, creams, lotions, ointments, skin patches, parenterals, oral liquids such as suspensions, solutions and emulsions, ophthalmic liquids and injectable liquids.

In one aspect, compositions of the present invention are prepared by admixture of an oligopeptide compound an appropriate anti-viral nucleoside analogue and a pharmaceutically acceptable carrier. As used herein, the expression "pharmaceutically acceptable" means acceptable for use in the pharmaceutical and veterinary arts, and not being toxic or otherwise unacceptable. The selection of carrier depends on the intended mode of administration of the composition. Thus, compositions to be administered orally are prepared using substances that are suitably combined with the oligopeptide and the nucleoside analogue for oral ingestion. Such substances include, without limitation, sugars, such as lactose, glucose and sucrose; starches such as corn starch and potato starch; cellulose and derivatives thereof, including sodium carboxymethylcellulose, ethylcellulose and cellulose acetates; powdered tragancanth; malt; gelatin; talc; stearic acids; magnesium stearate; calcium sulfate; vegetable oils, such as peanut oils, cotton seed oil, sesame oil, olive oil and corn oil; polyols such as propylene glycol, glycerine, sorbital, mannitol and polyethylene glycol; agar; alginic acids; water; isotonic saline and phosphate buffer solutions. Wetting agents, lubricants such as sodium lauryl sulfate, stabilizers, tabletting agents, anti-oxidants, preservatives, colouring agents and flavouring agents may also be present. Compositions to be administered by injection are prepared using liquid carriers such as buffers saline and physiological saline. Likewise, compositions for ophthalmic administration are prepared in suitable liquid carriers such as buffered or physiological saline. Creams, lotions and ointments may be prepared for topical application using an appropriate base such as triglyceride base. Such creams, lotions and ointments may also contain a surface active agent.

In treating a mammal having a viral infection, a therapeutically effective amount of the present composition is administered thereto in accordance with the present invention. The term "mammal" is meant to encompass, without limitation, humans, domestic animals such as dogs, cats, horses, cattle, swine, sheep, goats and the like, as well as wild animals. Further, as used herein, the term "therapeutically effective amount" is an amount of the composition indicated for treatment of the infection while not exceeding an amount which may cause significant adverse effects.

In a further and preferred aspect of the present invention, the anti-viral nucleoside analogue and anti-viral oligopeptide are administered concurrently in separate compositions rather than administered admixed in a single composition. This is particularly preferred when the desired mode of administration of the nucleoside analogue and the oligopeptide differ. Thus, a composition comprising an anti-viral nucleoside analogue is prepared by admixture of the analogue with at least one suitable pharmaceutically acceptable carrier as described above to achieve an anti-viral nucleoside analogue composition in the desired administrable form. Likewise, a composition comprising an anti-viral oligopeptide is prepared by admixture with at least one suitable pharmaceutically acceptable carrier to achieve an anti-viral oligopeptide composition in the desired administrable form. The nucleoside analogue and oligopeptide anti-viral compositions are administered concurrently at appropriate dosage levels, i.e. dosage levels determined to be suitable for co-administration in a single composition, to a mammal requiring treatment of a viral infection.

In this regard, a pharmaceutical combination in kit form may be provided which includes a pharmaceutical nucleoside analogue composition and a pharmaceutical oligopeptide composition. In such a kit, the nucleoside analogue and oligopeptide compositions may be in different administrable forms, for example, the nucleoside analogue composition may be in an orally administrable form such as tablet, pill, capsule or powder form, while the oligopeptide composition may be in a form suitable for administration by injection, i.e. in solution form.

It will be appreciated that the amount of nucleoside analogue in the composition will vary with the nucleoside analogue to be used which, in turn, will vary with the viral infection being treated, and the severity of the infection. The specific oligopeptide for inclusion in the composition will also have an effect on the amount of nucleoside analogue in the composition. Similarly, the amount of oligonucleotide in compositions according to the present invention, will vary with the specific oligopeptide and nucleoside analogue selected. Reference may be made to product monographs or to Pharmacopoeias, for example, Martindale, *The Extra Pharmacopoeia* Ed. J. E. F. Reynolds, The Pharmaceutical Press, London, 1982, to determine unit doses of nucleoside analogue typically administered in treating specific viral infections. Generally, the amount of anti-viral nucleoside analogue required to treat a given viral infection, when administered in conjunction with an anti-viral oligopeptide according to the present invention, will be less than the amount of nucleoside analogue administered independently to achieve a similar therapeutic effect due to the synergy existing between the nucleoside analogue and the anti-viral oligopeptide.

The relative amounts of nucleoside analogue and oligopeptide compound required to form a synergistic composition or combination according to the present invention are determined using bioassays conventional in the art. Thus, cells infected with a virus, against which a given nucleoside analogue is active, are subjected to varying concentrations of that nucleoside analogue in the presence of varying concentrations of oligopeptide compound. In this way, the various combinations of concentrations of nucleoside analogue and oligopeptide which form synergistic compositions can be determined. Thus, as specifically described herein, the relative amounts of the nucleoside analogue, acyclovir, and oligopeptide compound, acetyl-[D-Arg]$_9$-NH$_2$, required to form a synergistic composition for inhibiting herpesvirus are determined by incubating cells infected with herpesvirus in the presence of varying concentrations of acyclovir and oligopeptide. The effect of these combinations on the infected cells can be compared to the expected cumulative effect of the combination to determine whether the combination is synergistic. From these analyses, dosages effective to treat a virally-infected mammal can be determined in an established manner.

In accordance with the specific embodiments disclosed herein, appropriate dosages of acyclovir and oligopeptide for administration in the treatment of herpesvirus infections range from about 100 to about 5000 µg acyclovir in combination with from about 10 to about 1000 µg oligopeptide per kilogram mammalian body weight. Further, dosages of AZT and oligopeptide suitable for treating mammals infected with HIV, range from about 100 to about 1000 µg AZT per kilogram mammalian body weight and from about 10 to about 300 µg oligopeptide per kilogram mammalian body weight. Particularly preferred dosages of AZT and oligopeptide are those dosages at the lower end of these ranges. A specific example of a preferred dosage is about 100 µg AZT per kg administered in conjunction with about 50 µg oligopeptide per kg. It will be understood, however, that dosage levels that deviate slightly from the ranges provided may also be suitable in the treatment of a given viral infection.

Embodiments of the invention are described in the following specific examples which are not to be construed as limiting.

EXAMPLE 1

Synthesis of the acetyl-[D-Arg]$_9$-NH$_2$ oligopeptide

This compound was synthesized using p-methylbenzhydrylamine (MBHA) resin as the solid support to provide the C-terminal blocking amine on the resultant peptide. Synthesis proceeded using D-arginine residues in which the amino functionality was blocked with the t-BOC group, and the guanidino functionality was blocked with the Tos group. The coupling cycles and deprotection were performed as descried for the (L-Arg) nonamer in Example 1. Upon completion of the coupling cycles, the resin-bound peptide was treated with 20% acetic anhydride in acetonitrile to incorporate an acetyl protecting group at the N-terminus thereof. Liberation of peptide from the resin, and removal of Tos groups, were achieved by treatment with hydrofluoric acid, to yield the C-terminally amidated peptide. Following removal of hydrofluoric acid, the resin/peptide mixture was washed with diethyl ether and extracted with aqueous acetic acid. The crude peptide was lyophilized, and then purified by RP-HPLC fractionation as described in Example 1. High resolution mass spectrometry showed the product to be the desired acetyl-[D-Arg]$_9$-NH$_2$ oligopeptide.

EXAMPLE 2

Synergistic anti-viral effect of acyclovir and acetyl-[D-Arg]$_9$-NH$_2$

Acyclovir (obtained from Sigma) hereinafter referred to as "ACV", acetyl-[D-Arg]$_9$-NH$_2$ (hereinafter referred to as "4C"), and a combination of acyclovir and acetyl-[D-Arg]$_9$-NH$_2$ (ACV/4C) were tested for the ability to inhibit HSV replication in virally infected vero cells (continuous passage African Green Monkey Kidney cells (ATCC-CRL 1585). Initially, the vero cells (2×10$^5$ cells per well of microtiter plate) were maintained in 0.5 ml Dulbecco's Minimal Essential Media (DMEM), 10% fetal bovine serum (FBS) and 10 µg/ml gentamicin. Vero cells to be treated with 4C and ACV/4C were pretreated with 4C. 0.5 ml aliquots of 4C at 100 µM, 33.3 µM, 11.1 µM, 3.7 µM, 1.2 µM and 0.4 µM concentrations in DMEM and 10% FBS were added to the cell-containing wells which were then incubated in a CO$_2$ incubator at 37° C. for 24 hrs. Following the incubation, the growth media was removed from the cells and the cells were inoculated with 0.1 ml of HSV (30–50 pfu/well). The inoculated cells were incubated for 1 hr at 37° C. in a CO$_2$ incubator.

Solutions of varying 4C and ACV concentrations were prepared using a serial three-fold dilutions method. For 4C, a 100.0 µM solution of 4C was prepared in DMEM and 2% FBS. 3 ml of this solution was transferred to a first tube; 1 ml of this solution was transferred to a second tube containing 2 ml DMEM and 2% FBS; 1 ml from the second tube was transferred to a third tube containing 2 ml DMEM and 2% FBS. This procedure was repeated to obtain six tubes having the following 4C concentrations: 100 µM, 33.3 µM, 3.7 µM, 1.2 µM and 0.4 µM. ACV tubes were prepared in a similar manner with the initial concentration of ACV being 16.6 µg/µl in DMEM and 2% FBS. The resulting concentrations of ACV were as follows: 16.6 µg/µl, 5.6 µg/µl, 1.9 µg/µl, 0.6 µg/µl, 0.2 µg/µl and 0.06 µg/µl.

To the virally-infected cells to be tested with 4C alone, 4C of varying concentrations was added in 0.5 ml aliquots to the wells containing these cells i.e. 0.5 ml of 100 µM, 33.3 µM, 11.1 µM, 3.7 µM, 1.2 µM and 0.4 µM was added respectively to the wells along with 0.5 ml DMEM and 2% FBS. To the virally-infected cells to be tested with ACV alone, ACV of varying concentrations was added in 0.5 ml aliquots to the wells containing these cells i.e. 0.5 ml of 16.6 µg/µl, 5.6 µg/µl, 1.9 µg/µl, 0.6 µg/µl, 0.2 µg/µl and 0.06 µg/µl along with 0.5 ml media. To the virally-infected cells to be tested with 4C/ACV, 0.5 ml of decreasing concentrations of both 4C and ACV were added respectively to cell-containing wells numbered 1–6.

The cells were incubated for 2–3 days, or until there were approximately 30–50 plaques in the control wells i.e. wells to which 1.0 ml of media only was added prior to incubation. The medium was removed from the wells. The monolayers were stained in a conventional manner using 5% crystal violet, 10% acetic acid and 10% formalin in PBS (phosphate buffer). Subsequent to staining the plaques were counted.

Figure 1:
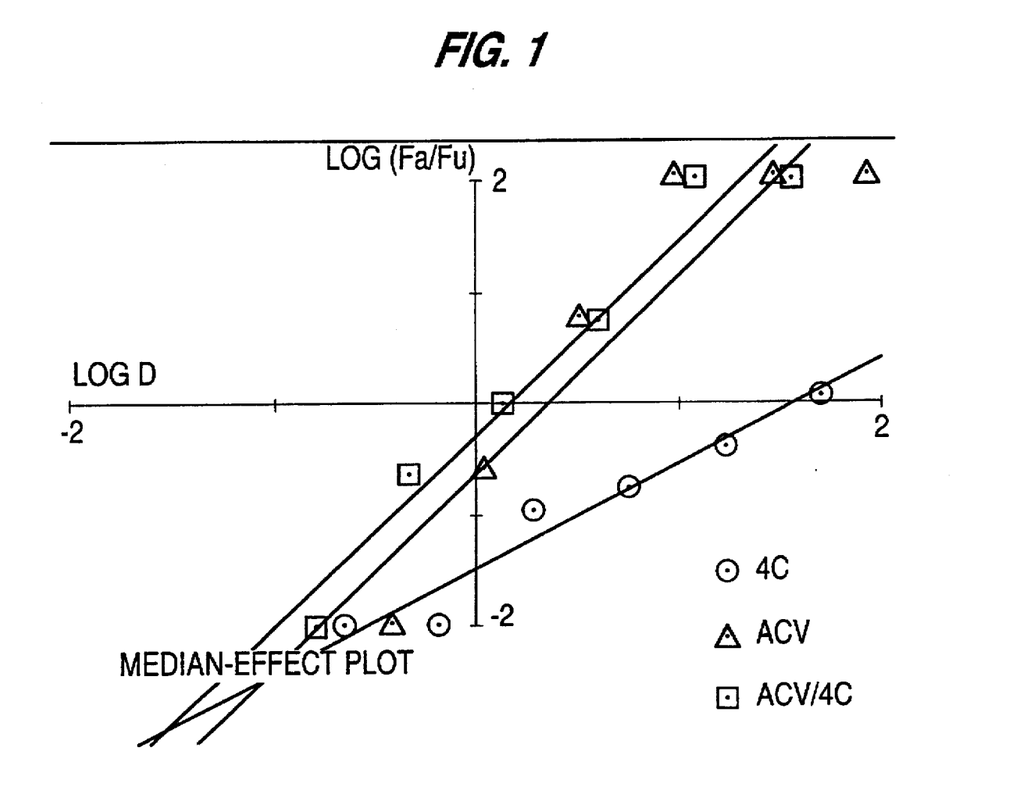
FIG. 1 is a median-effect plot for acyclovir, the 4C oligopeptide and the combination of acyclovir and the 4C oligopeptide.
Figure 2:
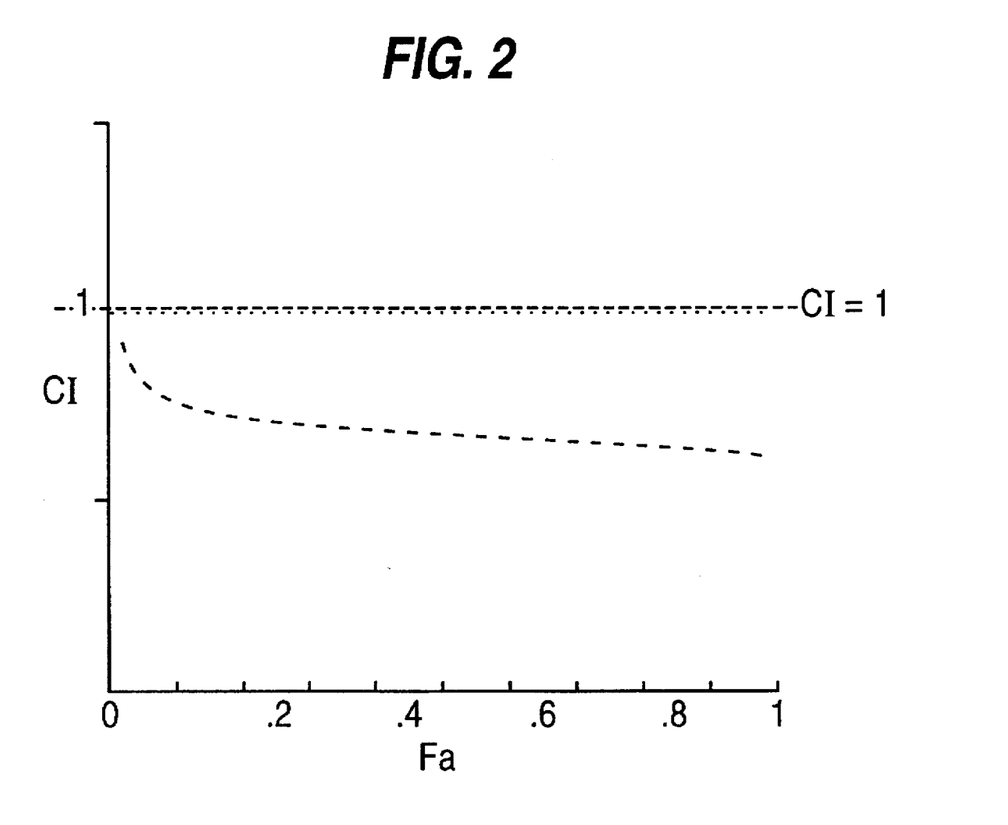
FIG. 2 is a plot of the combination index versus the affected cell fraction for the acyclovir/oligopeptide combination of FIG. 1.
Figure 3:
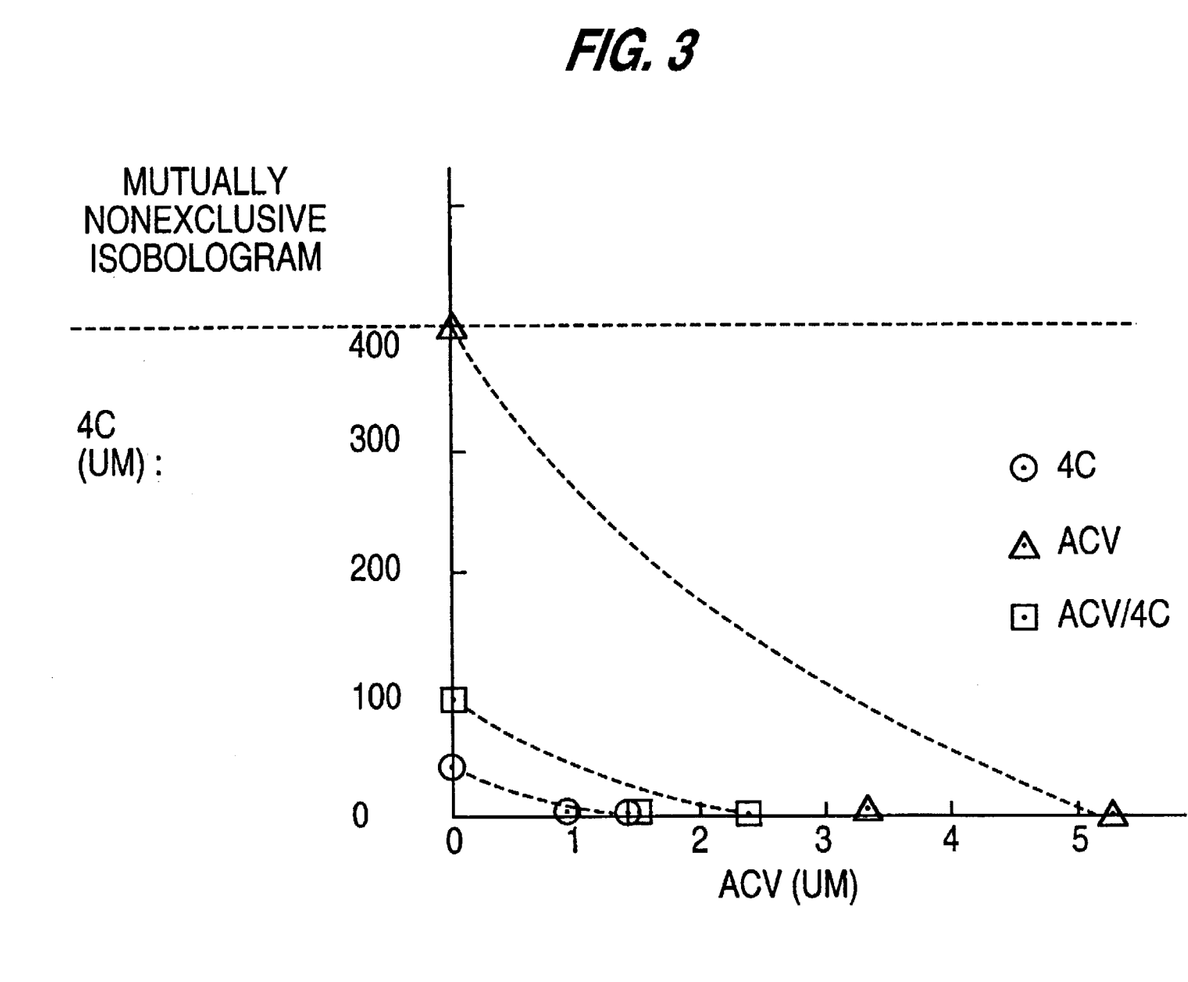
FIG. 3 is an isobologram of the acyclovir/oligopeptide combination characteristic of a synergistic combination.

A median-effect plot (FIG. 1) was prepared by plotting the log[dose of the drug] against log[fraction of cells affected by the drug($F_a$)]/[fraction of cells unaffected($F_u$)]. For the drug combination, the [dose of drug] is the sum of the doses of each drug. The combination index (CI) for the two drugs, i.e. ACV and 4C, is determined from the median-effect plot. A combination index of less than 1 indicates synergism. As shown in the $F_a$-CI plot of FIG. 2, the CI across the range of $F_a$ values for the ACV/4C combination is less than 1. Thus, the combination of ACV and 4C is synergistic in this range. Further, as shown in FIG. 3, an isobologram of the ACV/4C combination is also characteristic of a synergistic combination.

EXAMPLE 3

Synergistic anti-viral effect of AZT and acetyl-[D-Arg]$_9$-NH$_2$ (4C)

HUT-78 cells (1.75×10$^6$ cells), identified as ATCC TIB 161, were pretreated for 24 hours at 37° C. in 5% CO$_2$ in a 3.5 ml volume of maintenance media (RPMI 1640 media supplemented with 15% (v/v) heat inactivated fetal bovine serum, 25 nM HEPES, 2 g/l NaHCO$_3$ and 50 µg/ml gentamicin) containing various concentrations of 4C, i.e. 100 µM, 30 µM, 10 µM, 0.3 µM, 0.1 µM, 0.03 µM, 0.01 µM, 0.003 µM and 0.001 µM. Control cells were pretreated in 3.5 ml maintenance media under the same conditions.

The pretreated cells (1×10$^6$ cells, or 2 ml) of each 4C concentration were transferred to fresh tubes for viral adsorption. The tubes were centrifuged at 1200 rpm for 5 minutes to pellet the cells and each pellet was resuspended in 1 ml of stock HIV-1 strain NL4-3 (obtained from AIDS Research and Reference Reagent Program, Rockville, Md.) to obtain an MOI (multiplicity of infection) of about 0.05. The cells were incubated at 37° C. for 1 hour to allow viral adsorption to occur. The remaining 1.5 ml of pretreated cells of each 4C concentration were used for cytotoxicity controls. These cells were centrifuged as above, the resulting pellets were resuspended in 1 ml of media and incubated for 1 hour at 37° C. Following incubation, infected and non-infected cells were washed by centrifugation to remove unadsorbed virus and resuspended in 4C solution of appropriate concentration.

The following control and test wells were prepared:

| TYPE | DESCRIPTION |
| --- | --- |
| Media Control | Media |
| Cell Control | Media + uninfected untreated cells |
| Cytotoxicity Control | 4C + AZT + uninfected treated cells |
| Compound Color Control | 4C + AZT |
| Virus Control | Media + infected untreated cells |
| Test | 4C + AZT + infected treated cells |

AZT (Burroughs Wellcome Co.) thawed from sterile stock aliquots was serially diluted in media and dispensed at a volume of 100 µl per well of microtiter plate for the cytotoxicity control wells, compound color control wells and the test wells. Treated and untreated infected and uninfected cells were dispensed at a volume of 100 µl per well. The final concentrations of AZT in the wells was 100 nM, 300 nM, 100 nM, 30 nM and 10 nM following addition of cells.

The plates were incubated by 37° C. in 5% CO$_2$. On the third and sixth days of incubation, the media was changed by removing 100 µl of resuspended cells and replacing it in the Test and Cytotoxicity Control wells with 50 µl 4C and 50 µl AZT at appropriate concentrations and in the Cell and Virus Controls with 100 µl media. It was noted during these media changes that the 100 µM concentration of 4C was toxic to all cells, infected or not, both in the presence and absence of AZT.

On the 9th day, 20 µl supernatant was removed from above settled cells in the Test, Virus Control and Cell Control wells. The supernatant was assayed for the presence of p24 antigen using a Coulter Corporation p24 Antigen Test Kit in accordance with the manufacturer's directions.

Cell viability of the Cytotoxicity and Cell Control wells was determined using a microculture tetrazolium assay (MTA). The tetrazolium reagent used for this assay was 2,3-bis(2-methoxy-4-nitro-5-sulfophenyl)-5-[(phenylamino)carbonyl]-2H-tetrazolium hydroxide or XTT. Viable cells metabolize the XTT reagent and form a soluble formazan dye that is read at 450 nm following a 4 hour incubation at 37° C. The MTA was also preformed on the Color and Media Control wells in order that background color caused by 4C, AZT or the media can be subtracted from the reading.

Figure 4:
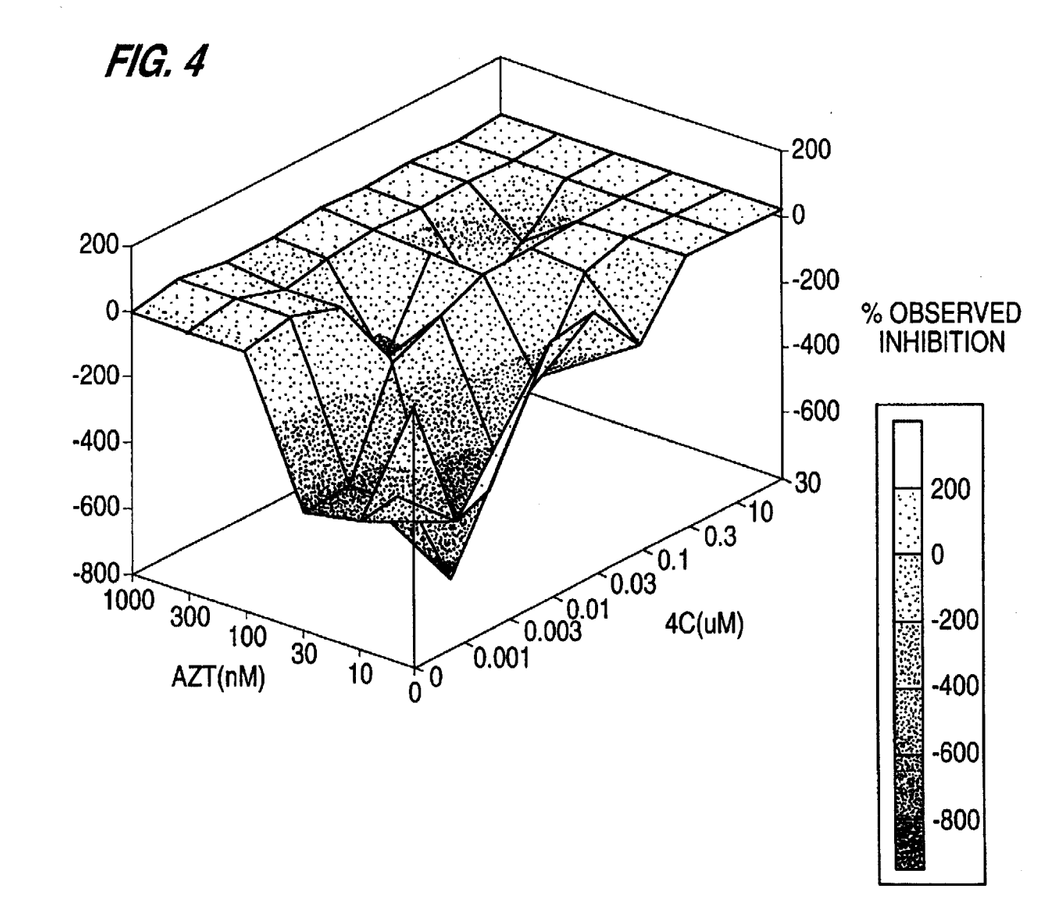
FIG. 4 is a 3-D plot of the inhibition observed against HIV-1 infected cells treated with AZT and the oligopeptide of FIG. 1.

The observed inhibition in the test wells was calculated as follows and plotted as shown in FIG. 4:

% Observed Inhibition=[(VC-Test)/(VC)]×100 where VC is the mean p24 of the Virus Control wells; and Test in the mean p24 of the Test wells.

Observed % inhibition was calculated to be as follows:

|  |  | Conc'n of 4C (μM) | | | | | | | |
| --- | --- | --- | --- | --- | --- | --- | --- | --- | --- |
|  |  | 0 | 0.001 | 0.003 | 0.01 | 0.03 | 0.1 | 0.3 | 10 | 30 |
| Conc'n of AZT (nM) | 1000 | −7.7 | 24.1 | 5.5 | 6.4 | 26.0 | 17.9 | 25.2 | 14.2 | 2.1 |
|  | 300 | −9.8 | 25.3 | −18.8 | −0.3 | 22.8 | 15.6 | 26.4 | 15.6 | 22.9 |
|  | 100 | −14.2 | 23.2 | −11.8 | −251.9 | 9.0 | −183.7 | −110.0 | 17.6 | 22.4 |
|  | 30 | −437.4 | −409.6 | −122.8 | −51.3 | 8.3 | 6.5 | 24.2 | 18.8 | 21.4 |
|  | 10 | −406.1 | −391.3 | −717.4 | −384.5 | −256.3 | 4.8 | 26.1 | 22.5 | 21.8 |
|  | 0 | 0.0 | −412.7 | −256.2 | −22.8 | 5.9 | −177.0 | 25.5 | 21.9 | 26.5 |

Figure 5:
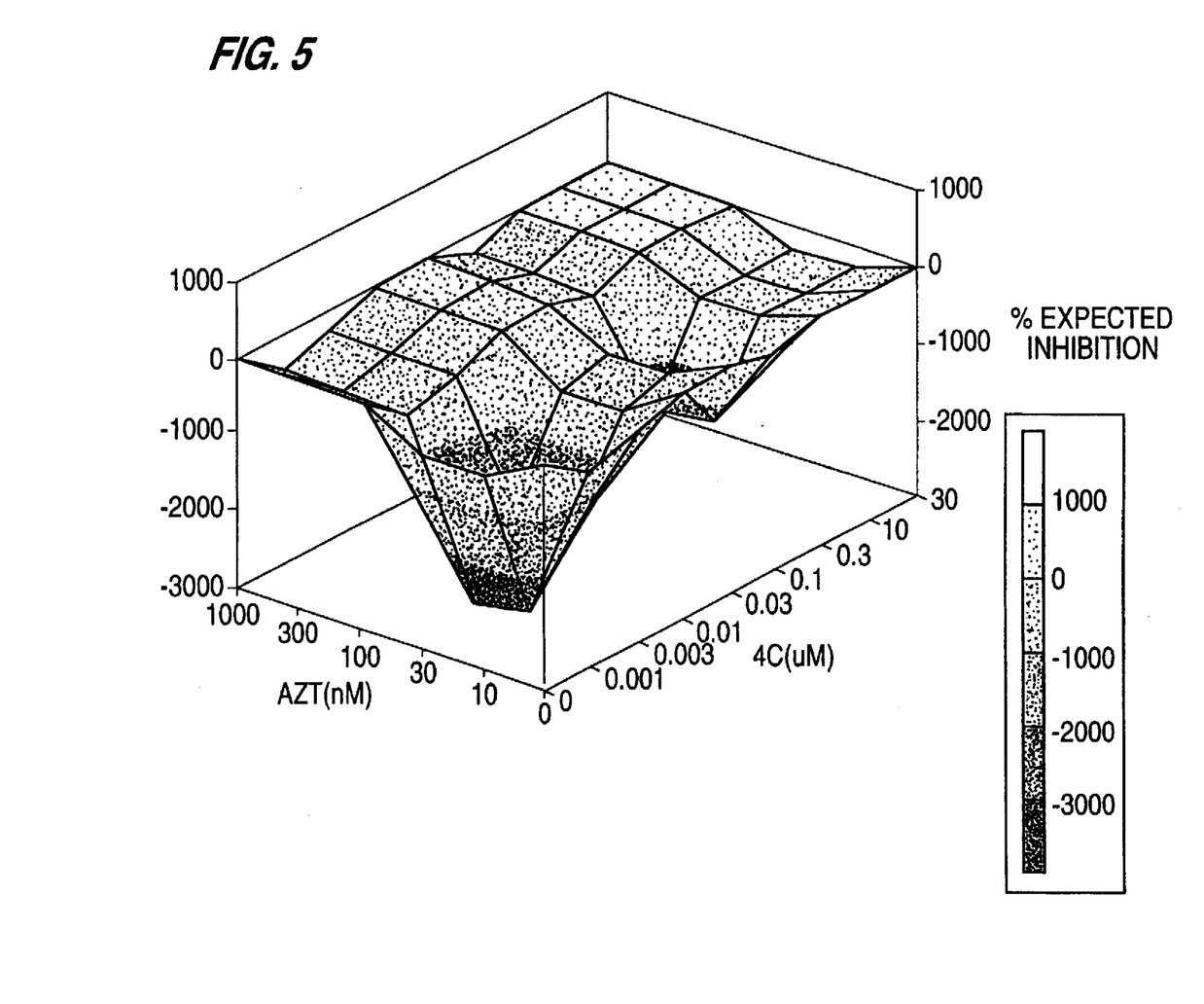
FIG. 5 is a 3-D plot of the inhibition expected against HIV-1 infected cells treated with AZT and the oligopeptide.

Expected inhibition (assuming and additive effect of 4C and AZT) was calculated as follows and plotted as shown in FIG. 5:

% Expected Inhibition=X+Y(100−X)

where X is observed % inhibition of 4C; and

Y is observed % inhibition of AZT.

Expected % inhibition was calculated to be as follows:

|  |  | Conc'n of 4C (μM) | | | | | | | |
| --- | --- | --- | --- | --- | --- | --- | --- | --- | --- |
|  |  | 0 | 0.001 | 0.003 | 0.01 | 0.03 | 0.1 | 0.3 | 10 | 30 |
| Conc'n of AZT (nM) | 1000 | −7.7 | −452.0 | −283.5 | −32.2 | −1.3 | −198.3 | 19.8 | 15.9 | 20.9 |
|  | 300 | −9.8 | −462.8 | −291.1 | −34.8 | −3.3 | −204.1 | 18.3 | 14.3 | 19.3 |
|  | 100 | −14.2 | −485.7 | −306.9 | −40.3 | −7.5 | −216.5 | 14.9 | 10.8 | 16.1 |
|  | 30 | −437.4 | −2654.9 | −1814.2 | −559.7 | −405.8 | −1388.6 | −300.1 | −319.7 | −294.8 |
|  | 10 | −406.1 | −2494.7 | −1702.9 | −521.4 | −376.4 | −1302.0 | −276.9 | −295.3 | −271.9 |
|  | 0 | 0.0 | −412.7 | −256.2 | −22.8 | 5.9 | −177.0 | 25.5 | 21.9 | 26.5 |

Figure 6:
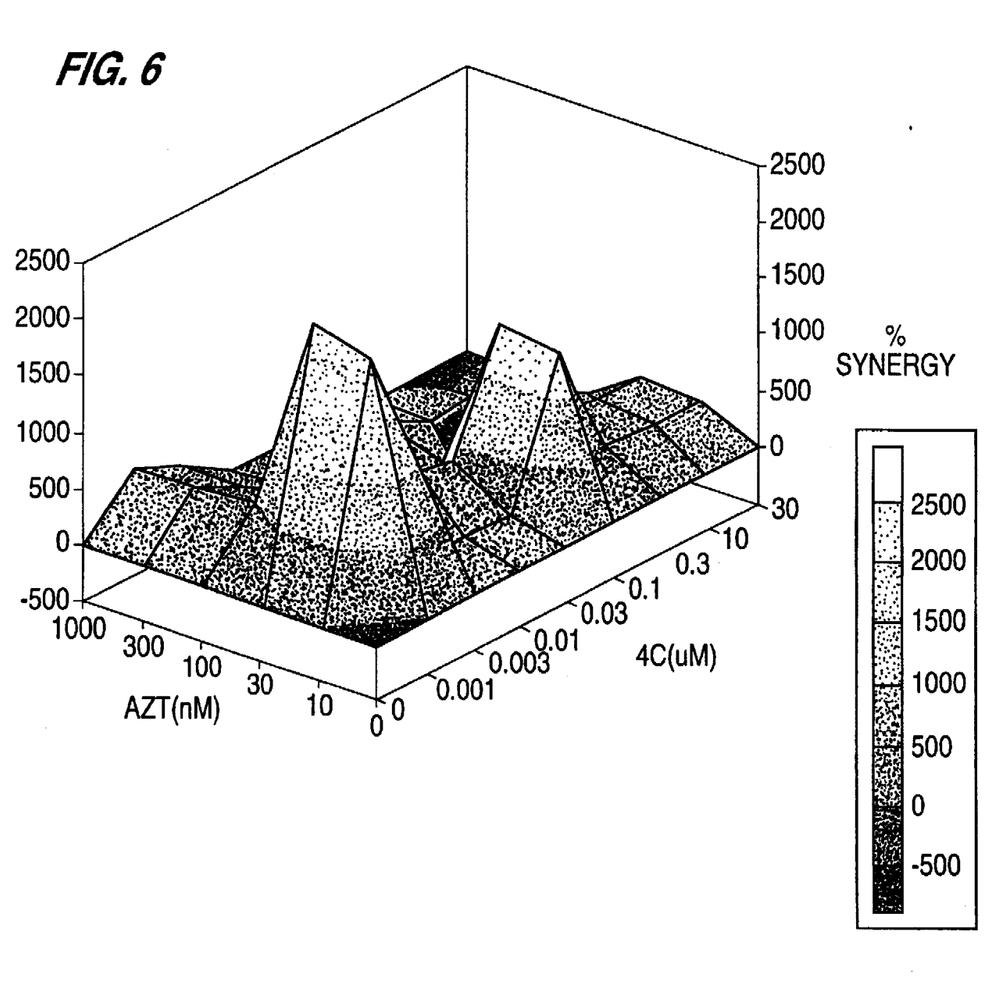
FIG. 6 is a 3-D plot illustrating the synergistic inhibitory effect of AZT and the anti-viral oligopeptide against HIV-1 infected cells.

The synergy plot (FIG. 6) shows the difference between the observed and expected % inhibition. Inhibition greater than that expected is due to synergy. As shown in FIG. 6, synergy is seen across the spectrum of the concentrations used of both 4C and AZT; however, synergy is particularly apparent at concentrations of about 10 to 100 nm AZT combined with about 0.001 to about 0.03 μM 4C and combined with about 0.1 to about 10 μM 4C respectively as seen by the peaks in these regions in FIG. 6.

We claim:

1. An anti-viral composition comprising at least one pharmaceutically acceptable carrier and a synergistic combination of 1) an anti-viral nucleoside analogue selected from the group consisting of dideoxyinosine, acyclovir, ganciclovir, penciclovir, famciclovir, azidothymidine, dideoxycytidine and 2'-deoxy-3'-thiacytidine; and 2) an anti-viral oligopeptide compound of the formula (I):

R1—[X]—R2  (I)

wherein X represents an oligopeptide consisting of from 6 to 12 D-arginine resides, R1 is H, lower alkanoyl or a deaminated amino acid, and R2 is OH, lower alkyl, —NH₂, N-(loweralkyl)amino, N,N-di-(loweralkyl)amino or a decarboxylated amino acid.

2. A composition as defined in claim 1, wherein X consist of 9 D-arginine residues.

3. A composition as defined in claim 2, wherein said oligopeptide compound is acetyl-(D-Arg)₉-NH₂.

4. A composition as defined in claim 3, wherein said nucleoside analogue is acyclovir.

5. A composition as defined in claim 3, wherein said nucleoside analogue is azidothymidine.

6. An anti-viral composition for treating a mammal infected with herpesvirus comprising at least one pharmaceutically acceptable carrier and a synergistic combination of 1) an anti-viral nucleoside analogue selected from the group consisting of acyclovir, ganciclovir, penciclovir, famciclovir, and 2) an anti-viral oligopeptide compound of the formula (I):

R1—[X]—R2  (I)

wherein X represents an oligopeptide consisting of from 6 to 12 D-arginine resides, R1 is H, lower alkanoyl or a deaminated amino acid, and R2 is OH, lower alkyl, —NH₂, N-(loweralkyl)amino, N,N-di-(loweralkyl)amino or a decarboxylated amino acid.

7. A pharmaceutical combination in kit form including:

1) an anti-viral nucleoside analogue selected from a group consisting of dideoxyinosine, acyclovir, ganciclovir, penciclovir, famciclovir, azidothymidine, dideoxycytidine and 2'-deoxy-3'-thiacytidine; and 2) an anti-viral oligopeptide compound of the formula (I):

R1—[X]—R2  (I)

wherein X represents an oligopeptide consisting of from 6 to 12 D-arginine resides, R1 is H, lower alkanoyl or a deaminated amino acid, and R2 is OH, lower alkyl, —NH₂, N-(loweralkyl)amino, N,N-di-(loweralkyl)amino or a decarboxylated amino acid.

8. A method of treating a herpesvirus infection in a mammal comprising administering to said mammal a combination of 1) an anti-viral nucleoside analogue selected from the group consisting of dideoxyinosine, acyclovir, ganciclovir, penciclovir, famciclovir, azidothymidine, dideoxycytidine and 2'-deoxy-3'-thiacytidine; and 2) an anti-viral oligopeptide compound of the formula (I):

R1—[X]—R2  (I)

wherein X represents an oligopeptide consisting of from 6 to 12 D-arginine resides, R1 is H, lower alkanoyl or a deaminated amino acid, and R2 is OH, lower alkyl, —$NH_2$, N-(loweralkyl)amino, N,N-di-(loweralkyl)amino or a decarboxylated amino acid.

9. A composition according to claim 1, wherein X represents a D-arginine homopolymer consisting of from 8 to 10 D-arginine residues.

10. A composition according to claim 6, wherein X represents a D-arginine homopolymer consisting of from 8 to 10 D-arginine residues.

11. A method of treating a herpesvirus infection in a mammal according to claim 8, wherein X represents a D-arginine homopolymer consisting of from 8 to 10 D-arginine residues.

12. A pharmaceutical combination in kit form a claimed in claim 7, wherein X represents a D-arginine homopolymer consisting of from 8 to 10 D-arginine residues.

13. A method of treating a herpesvirus infection in a mammal comprising administering to said mammal a combination of
   (1) an anti-viral nucleoside analogue selected from the group consisting of acyclovir, ganciclovir, penciclovir and famciclovir; and
   (2) the anti-viral oligopeptide acetyl-D-$(Arg)_9$-$NH_2$.

14. A method of treating a herpesvirus infection according to claim 13, wherein the anti-viral nucleoside analogue is acyclovir.

* * * * *